(12) United States Patent
Bialleck

(10) Patent No.: US 12,178,914 B2
(45) Date of Patent: *Dec. 31, 2024

(54) LYOPHILISATE OF TREOSULFAN

(71) Applicant: Medac Gesellschaft Für Klinische Spezialpräparate MBH, Wedel (DE)

(72) Inventor: Sebastian Bialleck, Wedel (DE)

(73) Assignee: Medac Gesellschaft Für Klinische Spezialpräparate MBH, Wedel (DE)

( * ) Notice: Subject to any disclaimer, the term of this patent is extended or adjusted under 35 U.S.C. 154(b) by 745 days.

This patent is subject to a terminal disclaimer.

(21) Appl. No.: 17/279,200

(22) PCT Filed: Sep. 25, 2019

(86) PCT No.: PCT/EP2019/075832
§ 371 (c)(1),
(2) Date: Mar. 24, 2021

(87) PCT Pub. No.: WO2020/064819
PCT Pub. Date: Apr. 2, 2020

(65) Prior Publication Data
US 2022/0031620 A1 Feb. 3, 2022

(30) Foreign Application Priority Data
Sep. 26, 2018 (EP) .................................. 18196967

(51) Int. Cl.
*A61K 9/19* (2006.01)
*C07C 309/08* (2006.01)

(52) U.S. Cl.
CPC .............. *A61K 9/19* (2013.01); *C07C 309/08* (2013.01); *C07B 2200/13* (2013.01)

(58) Field of Classification Search
CPC ...... A61K 35/39; A61K 35/545; A61K 38/28; A61K 9/1682; A61K 9/19; A61K 31/427; A61K 31/428; A61P 3/10; C07B 2200/13; C07C 309/08; C07D 471/04; C12N 2500/25; C12N 2500/32; C12N 2500/44; C12N 2501/16; C12N 2501/999; C12N 2506/02; C12N 2506/03; C12N 2506/45; C12N 2513/00; C12N 5/0606; C12N 5/0677; C12N 5/0696
See application file for complete search history.

(56) References Cited

U.S. PATENT DOCUMENTS 6,684,524 B1 2/2004 Sennhenn et al.
7,199,162 B1 4/2007 Baumgart

FOREIGN PATENT DOCUMENTS

| DE | 1188583 | 3/1965 |
|----|---------|--------|
| DE | 1193938 | 6/1965 |
| EP | 1227808 | 8/2002 |
| EP | 2599484 | 6/2013 |
| GB | 896052 | 5/1961 |
| GB | 891466 | 3/1962 |
| JP | 2003506654 | 2/2003 |
| JP | 2009526199 | 12/2012 |
| WO | 2007095033 | 8/2007 |
| WO | 2014127802 | 8/2014 |
| WO | WO2015/107534 | * 7/2015 |

OTHER PUBLICATIONS

International Search Report and Written Opinion in corresponding PCT/EP2019/075832, dated Dec. 12, 2019.
Baynes et al., "A phase 1 trial of escalating treosulfan in combination with high-dose melphalan and decarbazine (TMD) with peripheral blood progenitor cell transplant (PBPCT) in recurrent metastatic ovarian and breast cancer", Blood, 96(11), 2000.
Von Pawel, et al. "Clinical Phase II Trial of Treosulfan in Patients with Non-Resectable Non-Small-Cell Lung Cancer", Onkologie, 21, 1998, pp. 316-319.
International Preliminary Report on Patentability in corresponding PCT/EP2019/075832, dated Mar. 23, 2021.
Chekerov, et al., "Treosulfan in the Treatment of Advanced Ovarian Cancer—Results of a German Multicenter Non-interventional Study", Anticancer Research, 2015, 35, pp. 6869-6876.
Slatter, et al., "Treosulfan and Fludarabine Conditioning for Heniatopoietic Stern Cell Transplantation in Children with Primary Immunodefidency: UK Experience", Blol Blood Marrow Transplant, 2018, 24, pp. 529-536.
Robbins, et al., "Synthesis of Chiral Non-Racemic Diols From (S,S>-1,2,3,4-Diepoxyrütäne: (2S3S)-DffiYbröxy-I,4 Difhenylbutane", Orgaric Syntheses, 76, Jan. 1, 1999, p. I01.
Feit, "1,4-Bismetlianesulfoïïates of the Stereoisomeric Butanetetraols and Related Compounds", J Medicinal Chemistry, 7(1), Jan. 1, 1964, pp. 14-17.
Notice of Reasons for Refusal in corresponding Japanese Patent Application Serial No. 2021-516734, dated Oct. 5, 2022 (English machine translation attached), Date of drafting Sep. 30.
Notice of Reasons for Refusal in corresponding Japanese Patent Application Serial No. 2021-516733, dated Oct. 19, 2022 (English machine translation attached), Date of drafting Oct. 14.
Experimental Chemistry Course (Sequel), 2. Separation and Purification, Maruzen Inc., Jan. 25, 1967, pp. 159-178 and 186-187.
Ashizawa, et al., "Polymorphism and crystallization of the pharmaceutical drugs", Japan, Maruzen Planet Co., Ltd, 2002, pp. 3-16 and 273-278.
Takada, et al., "Drug Form screening and selection in the drug development phase", Pharm Stage, 2007, 10(6), pp. 20-25.
Yamano, et al., "Approach to Crystal Polymorph in Process Research of New Drug", Journal of Synthetic Organic Chemistry Japan, 2007, 65(9), pp. 907-913.

(Continued)

*Primary Examiner* — Yevgeny Valenrod
*Assistant Examiner* — Blaine G Doletski
(74) *Attorney, Agent, or Firm* — Hovey Williams LLP; Crissa A. Cook

(57) ABSTRACT

A lyophilisate of treosulfan is described which possesses favourable characteristics in terms of a short reconstitution time and a high purity and stability and which is particularly useful in the treatment of cancer and for conditioning therapy before transplantation of bone marrow or blood stem cells.

23 Claims, 3 Drawing Sheets

(56) References Cited

OTHER PUBLICATIONS

Mangin, et al., "Polymorphism in Processes of Crystallization in Solution: A Practical Review", Org. Process Res. Dev., 2009, 13(6), pp. 1241-1253.
The Japanese Pharmacopoeia, 16th Edition, 2011, p. 64-68 and 2070.
Kawakami, et al., "Formulation technology using amorphous state", Farumashia, 2016, 52(5), p. 402-406.
U.S. Food & Drug Administration, FDA, Guide to Inspections of Lypophilization of Parenterals [Japanese/English], Jun. 1993, pp. 1-31, retrieved from: https://www.ph-s.com/uploads/technical_documents/2009/06/tech200906_7.pdf.
Yonemochi Etsuo, "Effects of formulation factors on the crystal structure of freeze dried sugar alcohols", The Proceedings of Hoshi University, 2015, 201, No. 57, 1-9, (English abstract attached).
Notice of Final Rejection in corresponding Japanese Patent Application Serial No. 2021-516733, dated Apr. 24, 2023 (English translation attached).
Pre-Appeal Examination Report in corresponding Japanese Patent Application Serial No. 2021-516733, dated Nov. 9, 2023 (English translation attached).
Farumashia, "Table of contents/Special feature/Cover explanation", The Pharmaceutical Society of Japan, 2016, vol. 52 Issue 5, pp. 374-375 (English abstract attached).

\* cited by examiner

LYOPHILISATE OF TREOSULFAN

RELATED APPLICATIONS

This application is the U.S. National Stage of International Patent Application No., filed Sep. 25, 2019, which is hereby incorporated by reference in its entirety, and which claims priority to European Patent Application No. 18196967.6, filed Sep. 26, 2018.

The invention relates to a lyophilisate comprising the new crystalline form B of treosulfan, which lyophilisate has very favourable characteristics for use as a pharmaceutical composition and in particular can be quickly reconstituted to form ready-to-use solutions and shows a high stability and purity.

Treosulfan, chemical name (2S,3S)-(−)1,4-di(mesyloxy)-2,3-butanediol or L-Threitol-1,4-di(methanesulfonate), has the following chemical formula:

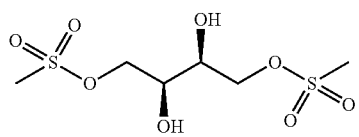 [SMILES: CS(=O)(=O)OC[C@H](O)[C@@H](O)COS(C)(=O)=O]

The chemical synthesis of treosulfan has been disclosed in DE 1 188 583 and DE 1 193 938 and is for example effected by reacting L-1,4-dibromobutane-2,3-diol and the silver salt of methanesulfonic acid.

Treosulfan is a dihydroxy derivative of busulfan and acts as an antineoplastic agent in view of its ability to alkylate the DNA. It is in use for the treatment of ovarian cancer either as such or in combination with further chemotherapeutics for example melphalan and dacarbazine (Baynes et al., Blood 96(11): 170a, Abstr. No. 731, 2000). For the treatment of ovarian cancer the monotherapy with treosulfan involves administering to the patient an amount of 8 g/m² body surface area, whereas the combination therapy with treosulfan and cisplatin involves administering treosulfan in an amount of 5 g/m².

Treosulfan has also been used in the treatment of advanced, non resectable non-small cell lung carcinomas (Pawel et al., Onkologie 21:316-319; 1998).

Furthermore, EP 1 227 808 A1 discloses the use of treosulfan in conditioning therapy before bone marrow or blood stem cell transplantation to a patient. In such conditioning therapy, the administration of treosulfan can effectively be combined with either administration of further agents, e.g. cyclophosphamid, carboplatin, thiotepa, melphalan, fludarabin, immune suppressive antibodies, or irradiation of the body. In comparison to the use of busulfan, serious side effects can predominantly or entirely be avoided. High dosages of treosulfan can even be used without causing serious liver, lung, kidney or CNS toxicities. The conditioning phase comprises a period of 2 to 7 days with a total dose of treosulfan of at least 20 g/m² body surface area before allogenic transplantation of bone marrow or haematopoietic stem cells.

Treosulfan is commercially available as capsules for oral use and a sterile powder consisting of treosulfan for preparing a solution for infusion. The solution is administered intravenously within about 15 to 30 minutes. The treosulfan in these products is a crystalline form exhibiting a powder X-ray diffraction pattern (XRPD) having characteristic peaks at 7.69, 15.43, 18.74, 19.14, 19.77, 20.15, 20.28, 21.24, 21.74, 22.07, 22.96, 23.24, 24.36, 25.29, 28.05, 28.28, 28.97, 30.10 and 40.55±0.2 degrees 2Θ. This crystalline form is in the following designated as form A and its XRPD pattern is shown in FIG. 2.

For preparing a solution for infusion, the commercial sterile powder is dissolved in e.g. in water to a concentration of 50 mg/ml and the obtained solution is diluted with e.g. isotonic NaCl solution. However, the water used as solvent has to be warmed to 30° C. for the reconstitution step. Moreover, the powder has to be completely removed from the walls of the vial. This step is important to avoid formation of powder particles which are sticking to the wall. Such sticky particles of form A of treosulfan are difficult to be dissolved and they protract the complete dissolution. The whole process for preparing a solution for infusion from the sterile powder, including the preparation of the vial, the necessary warming of water and the complete dissolution of the powder, takes about 10 minutes. Moreover, the use of warm solvent enhances the risk of undesired degradation.

WO 2015/107534 refers to two allegedly novel and distinct polymorphic forms of treosulfan, designated as form I and form II. The document lacks any indication whatsoever as to how form II can be obtained and hence lacks enabling disclosure for form II. The process for preparing form I is described only in a very general manner and is said to merely involve recrystallisation from organic solvents or mixtures thereof with some preferred organic solvents being mentioned. No disclosure of a specific process to prepare form I is provided. The x-ray powder diffraction pattern given for form I strongly resembles that of the crystalline form A of the commercially available product which is represented in FIG. 2 below suggesting these forms to be actually identical. Finally, WO 2015/107534 also describes lyophilized formulations which are said to typically include treosulfan of form I.

However, the known lyophilisates suffer from a couple of disadvantages. In particular, the known lyophilisates require long times for their reconstitution and their content of methanesulfonic acid and water, in particular after storage, is undesirably high and hence their purity and stability is not satisfactory. Moreover, the optimized lyophilisation process which has apparently been used leads to samples with properties varying to a large degree and hence lacks the desired reproducibility which is very problematic bearing in mind that these lyophilisates are intended to be used as pharmaceutical compositions.

Methanesulfonic acid (MSA) is a degradation product of treosulfan as is shown by the following reaction scheme.

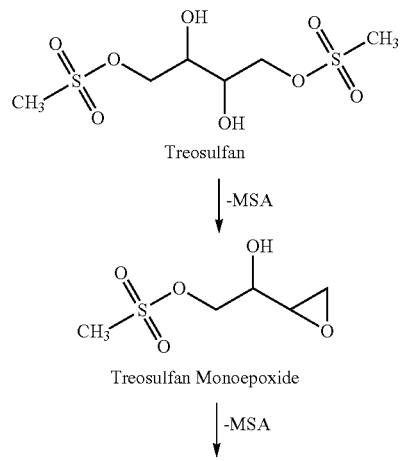

-continued

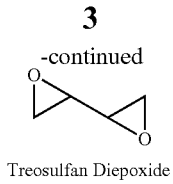

Treosulfan Diepoxide

Therefore, its presence indicates degradation of treosulfan. Due to its strong acidity it accelerates hydrolysis of the ester groups of treosulfan and thus enhances the degradation process. For this reason the amount of methanesulfonic acid should be as low as possible.

It is, therefore, an object of the present invention to avoid the disadvantages of the known products comprising treosulfan.

This object is achieved by the lyophilisate of treosulfan according to claims 1 to 10.

The invention also relates to the process for preparing the lyophilisate of treosulfan according to claims 11 to 21 and the lyophilisate of treosulfan for use in medicine according to claims 22 to 23.

DETAILED DESCRIPTION

The lyophilisate according to the invention is characterized in that it comprises crystalline form B of treosulfan exhibiting an X-ray powder diffraction pattern having characteristic peaks at 20.87 and 23.47±0.20 degrees 2Θ.

It is preferred that the crystalline form B exhibits an X-ray powder diffraction pattern having peaks at 20.87, 23.47, 26.20, 29.65, 30.81, 34.54, 35.30, 36.87 and 46.24±0.20 degrees 2Θ.

Figure 1:
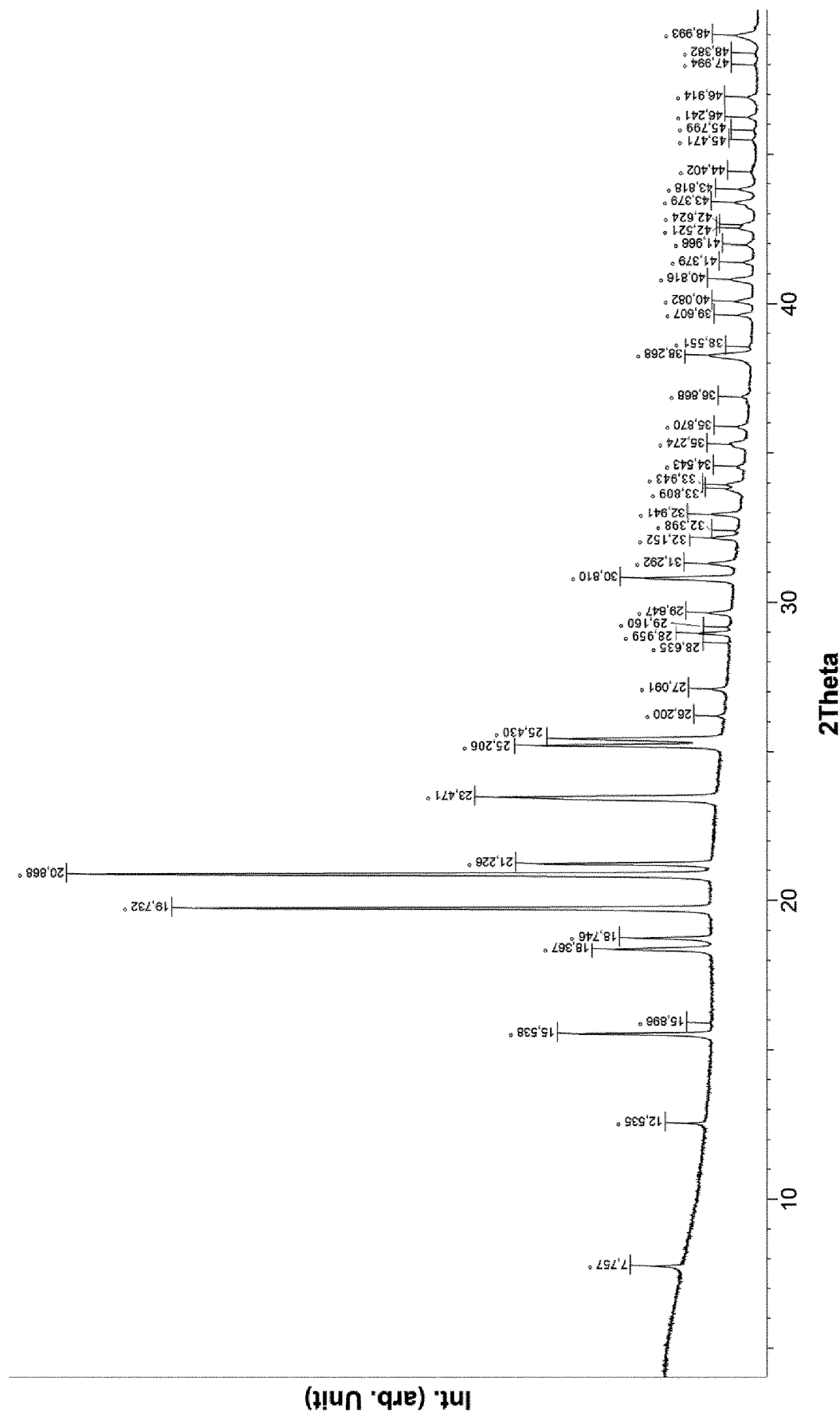
FIG. 1 shows an XRPD pattern of crystals of crystalline form B of treosulfan.

It is more preferred that the crystalline form B exhibits an X-ray powder diffraction pattern essentially as shown in FIG. 1.

It is even more preferred that the crystalline form B exhibits an X-ray powder diffraction pattern having no peaks in at least one, and preferably in all of the following regions a to f, expressed as degrees 2Θ:

| Region | Degrees 2Θ |
|--------|------------|
| a | 19.00–19.50 |
| b | 20.00–20.65 |
| c | 21.50–23.21 |
| d | 23.75–24.95 |
| e | 27.40–28.35 |
| f | 30.00–30.60 |

The crystalline form B is preferably also characterized by the space group and the parameters a, b, c, α, β, γ of the unit cell as well as the volume of the unit cell obtained by single-crystal x-ray diffraction (SCXRD) analysis, which structural data are given in the following table together with further information especially on the quality of the fit in comparison to those of the commercial form A.

|  | Form A | Form B (Invention) |
|---|---|---|
| Space group | orthorhombic, $P2_12_12_1$ | monoclinic, $P2_1$ |
| a | 5.5306 (5) Å | 5.5692 (9) Å |
| b | 8.9220 (8) Å | 8.9469 (15) Å |
| c | 22.8442 (18) Å | 11.322 (2) Å |
| α | 90° | 90° |
| β | 90° | 95.497 (16)° |
| γ | 90° | 90° |
| V | 1127.22 (17) Å$^3$ | 561.54 (17) Å$^3$ |
| Z/Z' | 4/1 | 2/1 |
| Final R indices (observed data, I > 2σ (I) ) | R1 = 0.0256, wR2 = 0.0462 | R1 = 0.0798, wR2 = 0.1956 |
| R indices (all data) | R1 = 0.0280, wR2 = 0.0471 | R1 = 0.0912, wR2 = 0.2065 |
| Goodness of fit | 0.966 | 1.163 |
| T | 173 (2) K | 173 (2) K | a, b and c=Lengths of edges of unit cell
α,β and γ=Angles between edges of unit cell
V=Volume of unit cell
Z/Z'=Number of molecules in unit cell
R1 and wR2=Confidence values
T=Temperature at which analysis has been carried out As can be seen from these data, form B has two molecules per unit cell (space group $P2_1$) and a volume of 561.5 Å$^3$, whereas form A has four molecules per unit cell (space group $P2_12_12_1$) and a volume of 1127.22 Å$^3$.

The lyophilisate according to the invention comprises in particular at least 96% by weight, preferably at least 97% by weight, more preferably at least 98% by weight and even more preferably at least 99% by weight of the crystalline form B, relative to the combined amount of crystalline form B and crystalline form A.

The lyophilisate according to the invention, therefore, comprises only very small amounts of the conventional crystalline form A and very high amounts of the crystalline form B. The high polymorphic purity is particularly advantageous for the use of the lyophilisate of the invention as a pharmaceutical composition.

In a further preferred embodiment, the lyophilisate according to the invention comprises at least 75% by weight, in particular at least 80% by weight, preferably at least 85% by weight, more preferably at least 90% by weight and even more preferably at least 95% by weight of the crystalline form B, relative to the amount of lyophilisate.

In yet another preferred embodiment the lyophilisate according to the invention comprises less than 20% by weight, in particular less than 15% by weight, preferably less than 10% by weight and more preferably less than 5% by weight of amorphous phase, relative to the amount of lyophilisate.

The small amount of amorphous phase avoids a couple of significant disadvantages associated with this phase. First of all, the amorphous phase tends to result in uncontrolled crystallization. In addition, it is more quickly degraded, has a higher residual moisture content after drying, shows inferior flowability and wettability and more easily becomes electrostatically charged. All of these properties are not desirable for a lyophilisate used for pharmaceutical purposes.

The lyophilisate according to the invention surprisingly shows a combination of advantageous properties which are assumed to be caused by the high amount of the crystalline form B of treosulfan. In particular, it requires only a very short time for complete dissolution in media usually employed for reconstitution to give ready-to-use injection or infusion solutions. Isotonic saline solution and water for injection are typically employed as such media. Other pharmaceutically acceptable solutions are also possible for the reconstitution, e.g. Ringer's lactate solutions or phosphate buffers. The very short period of time for reconstitution is very favourable since it enables clinic staff to prepare ready-to-use solutions freshly directly before the intended administration to patients, without having to allow for long waiting times for complete dissolution. Likewise, with such short reconstitution times, the risk of undesired degradation reactions of the treosulfan decreases.

Moreover, the lyophilisate according to the invention also has a high purity and stability as reflected by its very high content of the active ingredient treosulfan and a very small content of the degradation product methanesulfonic acid.

In a preferred embodiment, the lyophilisate according to the invention comprises at least 95% by weight, in particular at least 95% by weight, preferably at least 98% by weight and more preferably at least 99% by weight of treosulfan.

Further, the lyophilisate according to the invention has only a small methanesulfonic acid content and comprises in particular less than 0.2% by weight, preferably less than 0.1% and more preferably less than 0.05% by weight of methanesulfonic acid. The particularly small amount of methanesulfonic acid is one reasonable explanation for the high storage stability of the lyophilisate of the invention as this acid accelerates hydrolysis of the ester groups of treosulfan and therefore promotes its degradation.

Even after storing the lyophilisate for three months at 40° C. and a relative humidity of 75%, it comprises in particular less than 0.2% by weight, preferably less than 0.1% by weight and more preferably less than 0.05% by weight of methanesulfonic acid. This is an indicator for the excellent storage stability of the lyophilisate according to the invention making it very suitable for use as a pharmaceutical composition or a component thereof.

It is a further advantage of the lyophilisate according to the invention that it can be reconstituted using solvent having a temperature of about 20° C. thus dispensing with the need to employ pre-heated solvents. Furthermore, the cumbersome preparation to remove sticky clusters of the commercial form A from the vial wall before reconstitution is also not needed.

Moreover, the lyophilisate according to the invention has only a small water content and comprises water in an amount of in particular less than 1% by weight, preferably less than 0.5% by weight and more preferably less than 0.1% by weight, as determined by Karl Fischer titration.

The invention also relates to a process for preparing the lyophilisate. The process according to the invention comprises freeze-drying an aqueous solution comprising treosulfan.

The aqueous solution subjected to the freeze-drying is in the following also referred to as "pre-lyophilisation solution".

It is preferred that the aqueous solution comprises as solvent water or a mixture of water with at least one organic solvent. The organic solvent is in particular acetic acid.

The amount of water in the solvent is in particular 80 to 100% by weight and preferably 90 to 100% by weight. The amount of acetic acid in the solvent is in particular 1 to 20% by weight and preferably 2 to 10% by weight.

Even when using a pre-lyophilisation solution which comprises acetic acid, the obtained lyophilisate according to the invention surprisingly comprises only a very small amount of acetic acid and in particular less than 1.0% by weight, preferably less than 0.5% by weight and more preferably less than 0.2% by weight of acetic acid.

The aqueous pre-lyophilisation solution usually comprises treosulfan in a concentration of 50 to 150 mg/g, in particular 50 to 100 mg/g and more preferably 50 mg/g to 80 mg/g.

The pre-lyophilisation solution may also include additives such as solubilizers, e.g. polysorbate, cyclodextrins, sodium dodecyl sulfate, poloxamer and the like; chelating agents, e.g. sodium EDTA, DTPA, calteridol and the like; antioxidants, e.g. butylated hydroxy toluene, butylated hydroxy anisole, methionine, glutathione, metabisulfite sodium, alpha-tocopherol, thioglycolate sodium, cysteine, ascorbic acid and the like; pH adjusting agents and buffering agents, e.g. sodium hydroxide, hydrochloric acid, citric acid, sodium acetate, arginine, aspartic acid, sodium bicarbonate, sodium citrate, disodium citrate, trisodium citrate, maleic acid, sulfuric acid, hydrogen phosphate and the like; bulking agents, e.g. amino acids such as alanine and arginine and the like; sugar derivatives, e.g. example sucrose, dextrose, mannitol, trehalose, mannose and the like; or polymers, e.g. polyethylene glycol, gelatin, dextran and the like; stabilizers and tonicity adjusting agents e.g. as sodium chloride, magnesium chloride, sodium sulfate and the like.

Before subjecting the aqueous solution to the freeze-drying process, it is usually filtered employing conventional filters, e.g. a 0.22 µm filter, to obtain a sterile solution.

The freeze-drying of the pre-lyophilisation solution is typically effected by using freeze-drying machines normally employed for pharmaceutical purposes. As a rule, the solution is filled into suitable containers, such as vials, and the containers are placed in a conventional freeze-dryer with coolable and heatable surfaces on which the solution can be exposed to the various temperatures of the freeze-drying process. To achieve the drying, the solution is usually frozen and exposed to a decreased atmospheric pressure. As a result, sublimation of the solvent from the frozen solution takes place to a great extent, which precipitates for example on cooler regions of the freeze-dryer provided for this. This is then usually followed by a secondary drying at higher temperatures. After completion of the freeze-drying, the lyophilisate obtained is normally allowed to come to room temperature and the containers including the lyophilisate are sealed under sterile conditions.

In a preferred embodiment, the process according to the invention comprises
  (a) providing the aqueous solution having a first temperature,
  (b) freezing the aqueous solution, wherein the aqueous solution is cooled from the first temperature to a freezing temperature at a cooling rate of not more than 3 K/min, and
  (c) drying the frozen solution obtained in step (b) to give the lyophilisate.

It is surprising and very advantageous that the process according to the invention allows to use such a rather low cooling rate since higher cooling rates as employed by conventional processes require the use of very sophisticated equipment. The process according to the invention is therefore very economic.

Moreover, it is preferred that the cooling rate in step (b) is not more than 2 K/min, preferably not more than 1.5 K/min and more preferably not more than 1.3 K/min. In an alternative embodiment, the cooling rate in step (b) is in particular from 0.05 to 1.5 and preferably from 0.1 to 1.3 K/min.

The first temperature in the process of the invention is in particular from 15° C. to 95° C., preferably from 20° C. to 50° C. and more preferably from 25° C. to 35° C.

The freezing temperature employed in the process is in particular −40° C. or less, preferably from −60° C. to −40° C. and more preferably from −50° C. to −40° C.

The frozen solution is kept at the freezing temperature for in particular at least 1 hour, preferably 1 to 10 hours and more preferably 2 to 8 hours.

In a further preferred embodiment of the process, the drying in step (c) includes a primary drying which is carried out by subjecting the frozen solution to a temperature of −25° C. or higher, preferably a temperature of −15° C. to 0° C., and subjecting the frozen solution to a pressure of 0.03 to 1.0 mbar, preferably 0.1 to 0.6 mbar and more preferably 0.3 to 0.5 mbar.

In an alternative further preferred embodiment of the process, the drying in step (c) includes a primary drying which is carried out by subjecting the frozen solution to a temperature of 0° C. or higher, preferably a temperature of 0° C. to 60° C., more preferably a temperature of 20° C. to 60° C., even more preferably a temperature of 30° C. to 50° C., and subjecting the frozen solution to a pressure of 0.03 to 1.0 mbar, preferably 0.1 to 0.6 mbar and more preferably 0.3 to 0.5 mbar.

The primary drying is preferably carried out for at least 5 hours and in particular for at least 10 hours.

It is also preferred that after the primary drying a secondary drying is carried out by subjecting the product of the primary drying to a temperature of at least 30° C., preferably 30 to 50° C., and subjecting the product of the primary drying to a pressure of 0.03 to 1.0 mbar, preferably 0.1 to 0.6 mbar and more preferably 0.3 to 0.5 mbar.

The secondary drying is preferably carried out for at least 2 hours and in particular for at least 4 hours.

The process according to the invention allows to prepare lyophilisates with excellent properties in a highly reproducible manner which is a substantial advantage in comparison to the conventional processes which give products substantially differing in their properties.

The lyophilisate according to the invention also proves to be particularly useful in medicine. The invention, therefore, also relates to the lyophilisate according to the invention for use as a medicament. In a further embodiment, the invention also relates to the lyophilisate according to the invention for use in the treatment of cancer and in particular ovarian cancer. In yet another embodiment, the invention also relates to the lyophilisate according to the invention for use in conditioning therapy before transplantation of bone marrow or of blood stem cells.

In a further aspect, the invention also relates to the use of the lyophilisate according to the invention for treatment of cancer or for conditioning therapy before bone marrow or blood stem cell transplantation.

In yet another aspect, the invention also relates to a method of treating patients suffering from cancer or a method of conditioning patients before marrow or blood stem cell transplantation, which methods involve administering to the patients a solution made from the lyophilisate according to the invention.

The invention is explained in more detail below with reference to non-limiting examples which also include methods which are in particular suitable to determine the above-mentioned properties of the lyophilisate according to the invention and of the crystalline form B and A of treosulfan.

EXAMPLES

Methods and Apparatus

In the following, the methods are given which have been used for obtaining X-ray powder diffraction (XRPD) patterns, for investigations by means of single-crystal X-ray diffraction (SCXRD), for determining the amount of crystalline form B and crystalline form A and the amount of amorphous phase, and for determining the amount of treosulfan, acetic acid, methanesulfonic acid and water.

Moreover, the general procedure for preparing glass vials and for determining the reconstitution behaviour as well the apparatus used for freeze drying are also indicated below.

General Procedure—Preparing Glass Vials

Glass vials for lyophilization were rinsed before use with purified water and depyrogenized for 2 hours at 300° C. Lyophilization stoppers were autoclaved (121° C., 20 min, 2 bar) and dried for 7 hours at 110° C.

Freeze Dryer

Freeze drying was carried out in a freeze dryer GT 2 (Manufacturer: Hof Sonderanlagenbau (Lohra, Germany)) with 0.4 m$^2$ shelf area and 8 kg ice condenser capacity including means for differential pressure measurement.

X-Ray Powder Diffraction (XRPD)

The respective sample was introduced in a standard glass capillary (Ø=0.7 mm) after careful manual grinding with a pestle in a mortar. The X-ray powder diffraction pattern was recorded at room temperature using a Bruker D8 Advance Diffractometer (Cu-Kα1=1.54059 Å, Johansson primary beam monochromator, position sensitive detector) in transmission mode with rotation of the sample. Data were collected in the range of 3 to 50 degrees 2Θ. The tube voltage and current were set to 40 kV and 40 mA, respectively.

Single-Crystal x-Ray Diffraction (SCXRD)

Single crystal X-ray diffraction data were recorded using a "Rigaku Xcalibur, Sapphire2, large Be window" diffractometer equipped with an X-ray generator containing a molybdenum anode (Mo-Kα=0.71073 Å).

Determination of Amount of Form B and a by XRPD and Rietveld Analysis

For determining the amount of crystalline form B and A of treosulfan, a respective sample was introduced in a standard glass capillary (Ø=0.7 mm) after careful manual grinding with a pestle in a mortar. The X-ray powder diffraction pattern was recorded at room temperature using a Bruker D8 Advance diffractometer (Cu-Kα1=1.54059 Å, Johansson primary beam monochromator, position sensitive detector) in transmission mode with rotation of the sample. Data were collected in the range of 4 to 50 degrees 2Θ over a period of 4 h. The tube voltage and current were set to 40 kV and 40 mA, respectively. The obtained data were subjected to a quantitative Rietveld analysis by means of the TOPAS software.

Determination of Amount of Amorphous Phase by XRPD and Rietveld Analysis with Internal Standard For determining the amount of amorphous phase, a respective sample was mixed with 25% by weight of CaF$_2$ (Aldrich Chemistry, Lot #MKBP1959V, Calcium Fluoride anhydrous, 99.99%) as internal standard. After careful manual grinding with a pestle in a mortar, the mixture was introduced in a standard glass capillary (Ø=1.0 mm). The X-ray powder diffraction pattern was recorded at room temperature using a Bruker D8 Advance diffractometer (Cu-Kα1=1.54059 Å, Johansson primary beam monochromator, position sensitive detector) in transmission mode with rotation of the sample. Data were collected in the range of 4 to 50 degrees 2Θ over a period of 12 hours. The tube voltage and current were set to 30 kV and 30 mA, respectively. The obtained data were subjected to a quantitative Rietveld analysis by means of the TOPAS software.

Crystalline form A and crystalline form B were the only crystalline phases which could be identified.

Determination of Amount of Treosulfan by RP-HPLC

The amount of treosulfan in a respective sample was determined using reversed-phase high pressure liquid chromatography (RP-HPLC) as indicated in the following:

| HPLC Equipment | Agilent Technologies |
| --- | --- |
| Column | Luna C18 (2), 5 μm, 250 × 4.6 mm (phenomenex) |
| Mobile phase A | 720 ml diluent + 30 ml methanol Isocratic, 25 min |
| Flow rate | 0.8 ml/min |
| Column temperature | 40° C. |
| Injected volume | 20 μl |
| Diluent | 697 mg $K_2HPO_4$/1000 ml, pH 4.5 ($H_3PO_4$) |
| Detection | Refractive index detector |
| Reference solution | 50 mg/ml treosulfan in diluent |
| Sample Solution | 50 mg/ml treosulfan in solvent for reconstitution |

Determination of Amount of Methanesulfonic Acid by HILIC

The amount of methanesulfonic acid (MSA) was determined using Hydrophilic Interaction Liquid Chromatography (HILIC) as indicated in the following:

| HPLC Equipment | |
| --- | --- |
| Column | Nucleodur HILIC (250 × 4.6 mm, 3 μm) |
| Eluent | 10 mmol Ammonium formiate in $H_2O$/acetonitrile (7:93) (Vol/Vol) |
| Flow rate | 1.4 ml/min |
| Column temperature | 45° C. |
| Injected volume | 20 μl |
| Detector | 35° C. |
| Run time | 1.5 times the retention time of methanesulfonic acid |
| Detection | Refractive index detector |
| Reference solution 1 | Dissolve methanesulfonic acid in HPLC-grade water to a final concentration of 2.0 mg/ml |
| Reference solution 2 | Dilute reference solution 1 with eluent to 0.1 mg/ml. Reference solution 2 is used for quantification of methanesulfonic acid in the test solution. |
| Test solution | Dissolve sample to be tested in HPLC-grade water to a final concentration of 20 mg/ml |

Determination of Residual Acetic Acid Content by Headspace Gas Chromatography (HS-GC)

The amount of residual acetic acid was determined by HS-GC after esterification to ethyl acetate.

For sample preparation, the lyophilisate of one vial was reconstituted with water using 20 ml of water per 1 g of lyophilisate. 500 μl of the reconstituted sample were mixed with 100 μl saturated $NaHSO_4$-solution and 50 μl of ethanol in a GC-vial. The GC vial was tightly crimped. All samples were prepared in duplicates.

For preparation of standards, a stock solution of acetic acid of 1 mg/ml was prepared and diluted to 5 individual standards containing 25 μg/ml to 0.5 μg/ml in water. Each stock solution (500 μl) was mixed with 100 μl saturated $NaHSO_4$ solution and 50 μl of ethanol in a GC-vial.

| Standards: | c (HOAc) mg/ml | Stock solution μl | Water μl | $NaHSO_4$ μl | Ethanol μl |
| --- | --- | --- | --- | --- | --- |
| 0.05% | 0.025 | 125 | 375 | 100 | 50 |
| 0.02% | 0.01 | 50 | 450 | 100 | 50 |
| 0.01% | 0.005 | 25 | 475 | 100 | 50 |
| 0.005% | 0.0025 | 12.5 | 488 | 100 | 50 |
| 0.001% | 0.0005 | 2.5 | 498 | 100 | 50 |

Standards were prepared in duplicates.

The GC method for quantification of residual solvents was used to determine the amount of acetic acid in form of its ethyl ester (see Ph.Eur. 2.4.24 Identification and control of residual solvents: System A). The chromatographic conditions used to quantify the amount of ethyl acetate correspond to the USP 467 method for the determination of residual solvents.

The following gas chromatograph was used:

| Manufacturer | Hewlett Packard |
| --- | --- |
| Type | 6890 |
| Headspace sampler | 7694, Agilent Technologies |
| Detector | FID |
| N2 source | Nitrogen generator G1000E, Parker |
| H2 source | Hydrogen generator PGH2100 |

The gas chromatograph and the head sampler were operated at the following conditions:

| 6890N | | 7694 Headspace sampler | |
| --- | --- | --- | --- |
| GC oven program: | | Loop size | 1 ml |
| Initial Temperature | 35° C. | Oven | 85° C. |
| Initial time | 20 min | Transfer line | 120° C. |
| Rate | 25° C./min | Loop | 100° C. |
| Final temperature | 250° C. | Equilibration time | 30 min |
| Final time | 15 min | Vial pressure | 14 psi |
| Injection port: | Split, 160° C. | Pressurization | 0.15 min |
| | Splitless | Loop fill | 0.5 min |
| Detector | FID 270° C. Nitrogen makeup | Inject | 0.5 min |
| Carrier Gas Flow | Nitrogen 3.7 ml/min | | |

Reconstitution Behavior

The dissolution behavior of the lyophilisates was determined by adding water for injection or 0.45% by weight of aqueous NaCl solution at room temperature to give a final concentration of about 50 mg/ml. The reconstitution process was monitored with regard to dissolution time and behavior.

Determination of Amount of Water by "Karl Fischer Titration"

About 100 mg of the respective sample was weighed into a glass vial which was sealed with a crimp cap. The sample was transferred into the furnace of a Karl Fischer coulometer type 756, furnace sample processor 774, of Metrohm (Filderstadt, Germany) which was heated to 90° C. The septum of the cap was penetrated by an injection needle, and the generated water vapour was directly transferred into the titration chamber of the Karl Fischer coulometer via dry nitrogen. The measurement was repeated once. Empty glass vials were used for blank correction.

Example 1—Preparation of Lyophilisate of Crystalline Form B

The solution as given in the table below was prepared by weighing 8.0 g of treosulfan in a single use polypropylene (PP) beaker. The required amount of the solvent was added and the treosulfan was dissolved under gentle agitation until a clear solution was obtained. The complete dissolution was checked by visual control. Afterwards the solution was filtered using a 0.2 μm filter. The solution was filled into cleaned and depyrogenized glass vials of a nominal volume of 20 ml.

Composition of Pre-Lyophilization Solution, Target Dose 500 mg Treosulfan Per Vial

| Concentration of treosulfan | Solvent | Fill per vial |
|---|---|---|
| 50 mg/g | 90 wt. % water for injection and 10 wt. % acetic acid | 10.0 g |

The filled vials were partially stoppered and the samples were loaded into the freeze dryer and freeze-dried according to the following lyophilization cycle.

Lyophilization Cycle

| Step # | Description | Shelf temperature [° C.] | Ice condenser temperature [° C.] | Pressure [mbar] | Time step [h:min] |
|---|---|---|---|---|---|
| 1 | Loading | 25 | — | 1000 | 00:01 |
| 2 | Freezing ramp (1.17 K/min) | −45 | — | 1000 | 01:00 |
| 3 | Freezing | −45 | — | 1000 | 05:00 |
| 4 | Vacuum adjustment | −45 | −70 | 0.05 | 00:30 |
| 5 | Primary drying ramp (0.28 K/min) | −20 | −70 | 0.05 | 01:30 |
| 6 | Primary drying | −20 | −70 | 0.05 | 109:00 |
| 7 | Secondary drying ramp (0.25 K/min) | 40 | −70 | 0.05 | 04:00 |
| 8 | Secondary drying | 40 | −70 | 0.05 | 20:00 |

All lyophilisates obtained were identified by XRPD analysis as crystalline form B of treosulfan.

The lyophilisate cakes were well-formed and homogeneous without visible defects. The complete lyophilisate cakes dissolved in 10 ml water for injection at room temperature within less than 30 seconds applying gentle shaking. No pre-heating of the solvent was necessary. The removal of sticky particles adhering to the wall of the vial was also not necessary. The residual amount of water of the lyophilisates was below the limit of quantification of 0.005% by weight.

Properties of Lyophilisates

| Amount of water | Reconstitution time |
|---|---|
| Below limit of quantification | <30 s |

Examples 2 and 3—Preparation of Lyophilisate of Form B

The solutions as given in the table below were prepared by dissolving treosulfan in the respective solvent (30 min, 25° C., ultra-sonic bath). The obtained solutions were filtered and the filtered solutions were filled in cleaned and depyrogenized glass vials (10 vials per formulation) which were stoppered in lyophilization position and sealed in lyophilization bags.

Composition of Pre-Lyophilization Solution, Target Dose 500 mg Treosulfan Per Vial

| Example | Concentration of treosulfan | Solvent | Fill amount per vial |
|---|---|---|---|
| 2 | 70 mg/g | 98 wt. % water for injection and 2 wt. % acetic acid | 7.14 g |
| 3 | 70 mg/g | 94 wt. % water for injection and 6 wt. % acetic acid | 7.14 g |

The samples were loaded into the freeze dryer and lyophilized according to the following lyophilization cycle.

Lyophilization Cycle

| Step # | Description | Shelf temperature [° C.] | Ice condenser temperature [° C.] | Pressure [mbar] | Time step [h:min] |
|---|---|---|---|---|---|
| 1 | Loading | 25 | — | 1000 | 00:01 |
| 2 | Freezing ramp (0.01 K/min) | −45 | — | 1000 | 12:00 |
| 3 | Freezing | −45 | — | 1000 | 02:00 |
| 4 | Annealing ramp (0.67 K/min) | −25 | — | 1000 | 00:30 |
| 5 | Annealing | −25 | — | 1000 | 05:00 |
| 6 | Freezing ramp (0.67 K/min) | −45 | — | 1000 | 00:30 |
| 7 | Freezing | −45 | — | 1000 | 00:30 |
| 8 | Vacuum adjustment | −45 | −70° C. | 0.05 | 00:30 |
| 9 | Primary Drying ramp (0.28 K/min) | −20 | −70° C. | 0.05 | 01:30 |
| 10 | Primary Drying | −20 | −70° C. | 0.05 | 14:00 |
| 11 | Secondary Drying ramp (0.25 K/min) | 40 | −70° C. | 0.05 | 04:00 |
| 12 | Secondary Drying | 40 | −70° C. | 0.05 | 20:00 |

All lyophilisates tested were identified by XRPD analysis as crystalline form B of treosulfan.

For reconstitution testing, the vials were vented and opened and 10 ml of 0.45% by weight aqueous NaCl solution (room temperature) were added using a 10 ml volumetric pipette. The lyophilisate cakes of both examples 2 and 3 reconstituted within 1 min only. No pre-heating of the solvent was necessary. The removal of sticky particles adhering to the wall of the vial was also not necessary.

For all lyophilisates, only a very low amount of residual water was determined. Moreover, all samples were free of impurities and showed a similar and high treosulfan content. The acetic acid content was below the detection limit of the HS-GC analysis of 0.003 wt. %.

Properties of Lyophilisates

| Example | Amount of treosulfan [wt. %] | Amount of water [wt. %] | Amount of acetic acid [wt. %] | Reconstitution time |
|---|---|---|---|---|
| 2 | 100 | <0.1 | Below detection limit | 1 min |
| 3 | 100 | <0.1 | Below detection limit | 1 min |

Example 4—Preparation of Lyophilisate of Crystalline Form B

The solution as given in the table below was prepared by weighing 10 g of treosulfan in a 150 ml polypropylene (PP) beaker. The solvent was added and the treosulfan was dissolved under stirring at an ambient temperature of 22° C. The obtained solution was filled into cleaned and depyrogenized glass vials of a nominal volume of 20 ml.

Composition of Pre-Lyophilization Solution, Target Dose about 1000 mg Treosulfan Per Vial

| Concentration of treosulfan | Solvent | Fill per vial |
|---|---|---|
| 75 mg/g | 90 wt. % water for injection and 10 wt. % acetic acid | 13.3 g |

The vials were stoppered in lyophilization position and sealed in lyophilisation bags. The samples were loaded into the freeze dryer and lyophilized according to the following lyophilization cycle.

Lyophilization Cycle

| Step # | Description | Shelf temperature [° C.] | Ice condenser temperature [° C.] | Pressure [mbar] | Time step [h:min] |
|---|---|---|---|---|---|
| 1 | Loading | 45 | — | atm. | 00:20 |
| 2 | Cooling ramp (0.23 K/min) | 15 | — | atm. | 02:10 |
| 3 | Isothermal incubation | 15 | — | atm. | 06:00 |
| 4 | Freezing ramp (0.3 K/min) | −45 | — | 1000 | 03:20 |
| 5 | Freezing | −45 | — | 1000 | 05:00 |
| 6 | Annealing ramp (1.33 K/min) | −5 | — | 1000 | 00:30 |
| 7 | Annealing | −5 | — | 1000 | 05:00 |
| 8 | Freezing ramp (0.4 K/min) | −45 | — | 1000 | 01:40 |
| 9 | Freezing | −45 | — | 1000 | 00:30 |
| 10 | Vacuum adjustment | −45 | −70 | 0.05 | 00:30 |
| 11 | Primary Drying ramp (0.44 K/min) | −5 | −70 | 0.05 | 01:30 |
| 12 | Primary Drying | −5 | −70 | 0.05 | 70:00 |
| 13 | Secondary Drying ramp (0.19 K/min) | 40 | −70 | 0.05 | 04:00 |
| 14 | Secondary Drying | 40 | −70 | 0.05 | 20:00 |

"atm." means atmospheric pressure

All lyophilisates tested were identified by XRPD analysis as crystalline form B of treosulfan.

The obtained lyophilisate cakes were acceptable. For reconstitution testing, the vials were vented and opened and 20 ml of 0.45% by weight aqueous NaCl solution (about 22° C.) were added. The lyophilisate cakes reconstituted within 1.5 min. No pre-heating of the solvent was necessary. The removal of sticky particles adhering to the wall of the vials was also not necessary.

All samples were free of impurities and had a very high content of treosulfan. The acetic acid content was very low.

Properties of Lyophilisates

| Amount of treosulfan [wt. %] | Amount of acetic acid [wt. %] | Reconstitution time |
|---|---|---|
| 100 | 0.07 | 1.5 min |

Example 5—Preparation of Lyophilisate of Crystalline Form B

A pre-lyophilization solution was prepared by mixing 52.5 g of treosulfan and 603.75 g of water under stirring at a temperature of 30° C. Stirring was continued for 30 minutes until complete dissolution of the treosulfan. After filtration using a 0.2 μm membrane filter, the filtered solution was filled into cleaned and depyrogenized glass vials.

Composition of Pre-Lyophilization Solution, Target Dose 5000 mg Treosulfan Per Vial

| Concentration of treosulfan | Solvent | Fill per vial |
|---|---|---|
| 80 mg/g | Water for injection | 62.5 g |

The vials were stoppered in lyophilization position and sealed in lyophilization bags. The samples were loaded into the freeze dryer and lyophilized according to the following lyophilization cycle.

Lyophilization Cycle

| # | Step Description | Shelf temperature [° C.] | Ice condenser temperature [° C.] | Pressure [mbar] | Time step [h:min] |
|---|---|---|---|---|---|
| 1 | Loading | 30 | — | atm. | 00:01 |
| 2 | Freezing ramp (1.0K/min) | −45 | — | atm. | 01:15 |
| 3 | Freezing | −45 | — | atm. | 03:00 |
| 4 | Annealing ramp (1.14K/min) | −5 | — | atm. | 00:35 |
| 5 | Annealing | −5 | — | atm. | 02:00 |
| 6 | Freezing ramp (1.14K/min) | −45 | — | atm. | 00:35 |
| 7 | Freezing | −45 | — | atm. | 01:00 |
| 8 | Vacuum adjustment | −45 | −70 | 0.38 | 00:30 |
| 9 | Primary Drying ramp (1.0K/min) | 40 | −70 | 0.38 | 01:25 |
| 10 | Primary/Secondary Drying | 40 | −70 | 0.38 | 77:00 |

"atm." means atmospheric pressure

The lyophilisates obtained were identified by XRPD analysis as crystalline form B of treosulfan.

The obtained lyophilisate cakes were homogenous without any defects. For reconstitution testing, the vials were vented, opened and 100 ml of 0.45% by weight aqueous NaCl solution (room temperature) were added to give a final concentration of treosulfan of 50 mg/ml. The lyophilisate cakes reconstituted within 30 seconds only. No pre-heating of the solvent was necessary. The removal of sticky particles adhering to the wall of the vials was also not necessary.

All lyophilisates showed a very high amount of treosulfan and a very low amount of residual water.

Properties of Lyophilisates

| Amount of treosulfan [% by weight] | Amount of Water [% by weight] | Reconstitution time |
|---|---|---|
| 99.97 | 0.04 | 30 S |

A sample of the lyophilisate was stored at 80° C. for 96 h. The stored sample still showed a very high content of treosulfan of >99.4% by weight. The methanesulfonic acid content was lower than 0.05% at the beginning of the testing and 0.05% after the storage proving the lyophilisate to be very stable.

Properties of Lyophilisate after Storage at 80° C. for 96 h

| Time | Amount of treosulfan [% by weight] | Amount of methanesulfonic acid [% by weight] |
|---|---|---|
| 0 h | 100.3 | <0.05 |
| 96 h | >99.4 | 0.05 |

Example 6—Preparation of Lyophilisate of Crystalline Form B

The solution of the composition as given in the table below was prepared by weighing water into a glass beaker and adjusting its temperature to 20° C. using a water bath. The corresponding amount of treosulfan was added and the mixture was stirred until complete dissolution. The obtained solution was filtered and the filtered solution was immediately filled into cleaned and depyrogenized glass vials which were tempered at 20° C.

Composition of Pre-Lyophilization Solution, Target Dose about 1000 mg Treosulfan Per Vial

| Concentration of treosulfan | Solvent | Fill per vial |
|---|---|---|
| 56 mg/g | Water | 17.95 g |

The vials were stoppered in lyophilisation position and sealed in lyophilization bags. The samples were loaded into the freeze dryer and lyophilized according to the following lyophilisation cycle.

Lyophilization Cycle

| # | Step Description | Shelf temperature [° C.] | Ice condenser temperature [° C.] | Pressure [mbar] | Time step [h:min] |
|---|---|---|---|---|---|
| 1 | Loading | 20 | — | atm. | 00:01 |
| 2 | Cooling ramp (0.3K/min) | 15 | — | atm. | 00:17 |
| 3 | Isothermal incubation | 15 | — | atm. | 06:00 |
| 4 | Freezing ramp (0.3K/min) | −45 | — | 1000 | 03:20 |
| 5 | Freezing | −45 | — | 1000 | 05:00 |
| 6 | Annealing ramp (0.1° C./min) | −15 | — | 1000 | 00:30 |
| 7 | Annealing | −15 | — | 1000 | 05:00 |
| 8 | Freezing ramp (0.3K/min) | −45 | — | 1000 | 01:40 |
| 9 | Freezing | −45 | — | 1000 | 00:30 |
| 10 | Vacuum adjustment | −45 | −70 | 0.05 | 00:30 |
| 11 | Primary Drying ramp | −5 | −70 | 0.05 | 01:30 |
| 12 | Primary Drying | −5 | −70 | 0.05 | 70:00 |
| 13 | Secondary Drying ramp | 40 | −70 | 0.05 | 04:00 |

-continued

| Step | | Shelf temperature | Ice condenser temperature | Pressure | Time step |
|---|---|---|---|---|---|
| # | Description | [° C.] | [° C.] | [mbar] | [h:min] |
| 14 | Secondary Drying | 40 | −70 | 0.05 | 20:00 |

The lyophilisates obtained were identified as form B of treosulfan by XRPD analysis.

All lyophilisates showed a very high content of treosulfan and a very low amount of residual water. Furthermore, the amount of methanesulfonic acid was also very low.

Properties of Lyophilisates

| Amount of treosulfan [% by weight] | Amount of water [% by weight] | Amount of methanesulfonic acid [% by weight] |
|---|---|---|
| 99.95 | 0.09 | <0.05 |

Samples of the lyophilisates were stored at 60° C. for 30 days, 70° C. for 18 days and 80° C. for 5 days. Irrespective of the storage conditions, at the end of the tests all samples dissolved completely within 1.5 minutes in 20 ml 0.45% by weight of aqueous NaCl solution. No pre-heating of the solvent was necessary. The removal of sticky particles adhering to the wall of the vials was also not necessary.

Moreover, all samples still showed a very high content of treosulfan.

Properties of Lyophilisates after Storage at 60 to 80° C.

| t [d] | T [° C.] | Amount of treosulfan [% by weight] | Reconstitution time |
|---|---|---|---|
| 0 | — | 99.95 | |
| 30 | 60 | 99.82 | 1.5 min |
| 18 | 70 | 99.94 | 1.5 min |
| 5 | 80 | 99.94 | 1.5 min |

Samples of the lyophilisates were also stored at 40° C. and 75% relative humidity (r.H.) for 3 months. All stored samples still showed a very high content of treosulfan and a very low amount of methanesulfonic acid indicating their excellent stability.

Properties of Lyophilisates after Storage at 40° C./75% r.H

| Time [months] | T/r.H. [° C./%] | Amount of treosulfan [% by weight] | Amount of methanesulfonic acid [% by weight] |
|---|---|---|---|
| 3 | 40/75 | >99.95 | <0.05% |

Example 7—Preparation of Lyophilisate of Crystalline Form B

The pre-lyophilization solution of the composition as given in the table below was prepared by weighing water into a glass beaker and adjusting its temperature to 30° C. using a water bath. The corresponding amount of treosulfan was added and the mixture was stirred at 30° C. for 30 min. The obtained solution was filtered and the filtered solution was immediately filled into cleaned and depyrogenized glass vials which were tempered at 30° C.

Composition of Pre-Lyophilization Solution, Target Dose about 5000 mg Treosulfan Per Vial

| Concentration of treosulfan | Solvent | Fill per vial |
|---|---|---|
| 80 mg/g | Water for injection | 62.5 g |

The vials were stoppered in lyophilisation position and sealed in lyophilization bags. The samples were loaded into the freeze dryer and lyophilized according to the following lyophilization cycle.

Lyophilization Cycle

| | Step | Shelf temperature | Ice condenser temperature | Pressure | Time step |
|---|---|---|---|---|---|
| # | Description | [° C.] | [° C.] | [mbar] | [h:min] |
| 1 | Loading | 30 | — | 1000 | 00:01 |
| 2 | Freezing ramp (1.17K/min) | −45 | — | 1000 | 01:04 |
| 3 | Freezing | −45 | — | 1000 | 06:00 |
| 4 | Annealing ramp (1K/min) | −10 | — | 1000 | 00:35 |
| 5 | Annealing | −10 | — | 1000 | 06:00 |
| 6 | Freezing ramp (1K/min) | −45 | — | 1000 | 00:35 |
| 7 | Freezing | −45 | — | 1000 | 03:00 |
| 8 | Vacuum adjustment | −45 | ≤−70 | 0.33 | 00:30 |
| 9 | Primary Drying ramp (0.94K/min) | 35 | ≤−70 | 0.33 | 01:25 |
| 10 | Primary Drying | 35 | ≤−70 | 0.33 | 62:00 |

The obtained lyophilisate cakes were homogenous without any defects. For reconstitution testing, the vials were vented, opened and 100 ml of 0.45% by weight aqueous NaCl solution (room temperature) were added to give a final concentration of treosulfan of 50 mg/ml. The lyophilisate cakes reconstituted within 30 seconds only. No pre-heating of the solvent was necessary. The removal of sticky particles adhering to the wall of the vials was also not necessary.

All lyophilisates showed a very low amount of residual water and a very low amount of methanesulfonic acid. The latter was even below the limit of detection (LOD) of 0.01% by weight.

Properties of Lyophilisates

| Amount of treosulfan [% by weight] | Amount of water [% by weight] | Amount of methanesulfonic acid [% by weight] | Reconstitution time |
|---|---|---|---|
| 101.79 | 0.01 | <LOD | 30 s |

The lyophilisates obtained were also subjected to XRPD analyses using Rietveld refinement to determine their crystallinity as well as their amount of form A, form B and amorphous phase. Crystalline form A and B were the only crystalline phases which could be detected. The results are given in the following table.

Results of XRPD Analyses

| Amount of crystalline treosulfan | Amount of form A and B | | Amount of amorphous phase [% by weight] |
|---|---|---|---|
| | [% by weight] Form A | [% by weight] Form B | |
| 96.3 | 0.5 | 99.5 | 3.7 |

Figure 3:
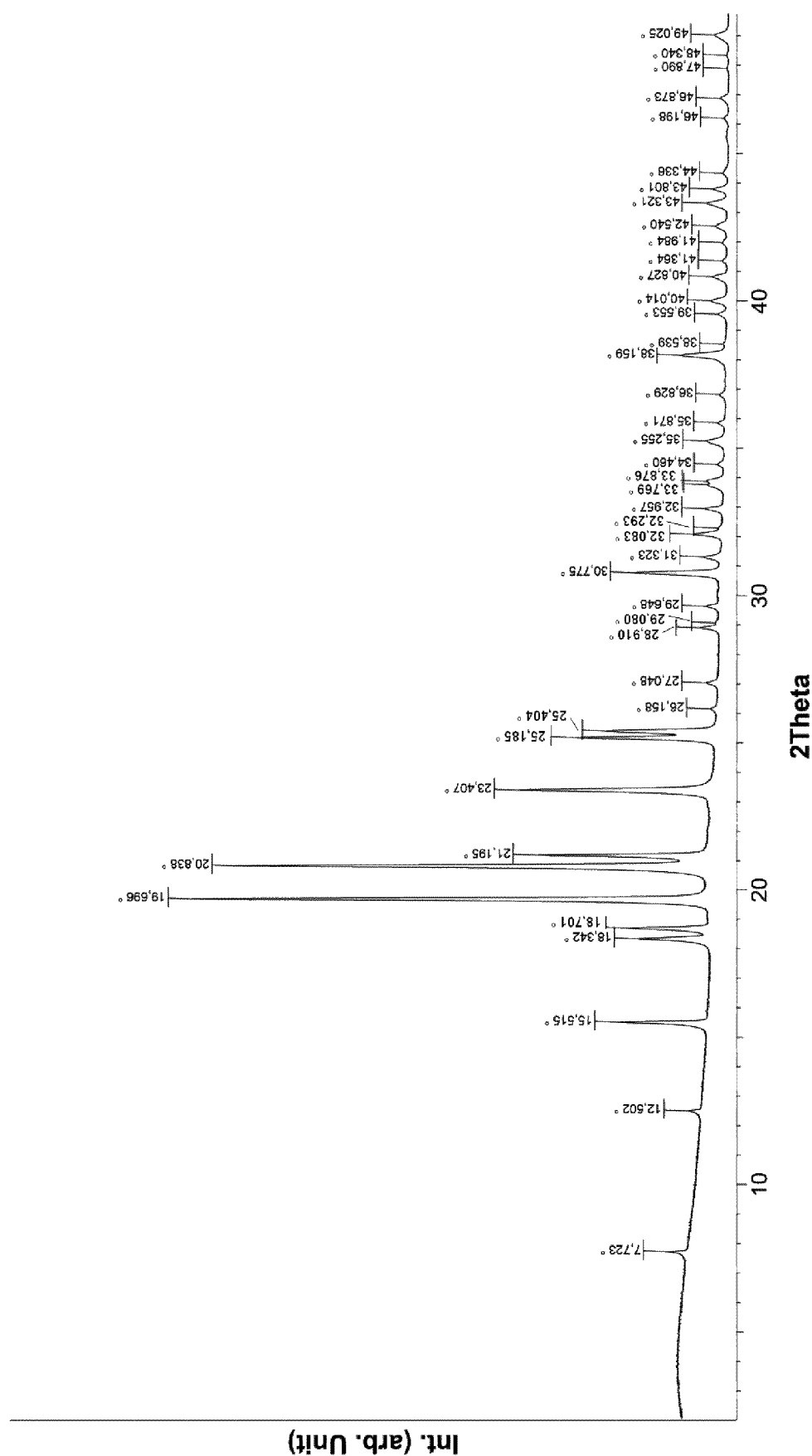
FIG. 3 shows an XRPD pattern of a lyophilisate of crystalline form B of treosulfan.

The XRPD pattern of the lyophilisates is shown in FIG. 3.

Example 8—Preparation of Crystalline Form B 99.8 mg treosulfan were weighed in a vial (volume 4.0 ml) which was equipped with a PTFE (Polytetrafluoroethylene) sealing and a stirrer. 1.5 ml of a mixture of 80 wt. % water and 20 wt. % isopropanol preheated to 65° C. were then added. The resulting solution was completely taken up with a syringe (volume 5 ml) and filtered using a 0.2 μm filter into a second vial (volume 4.0 ml). The syringe, second vial and filter had been tempered at 65° C. before use. The solvents were allowed to evaporate from the open vial at room temperature to dryness which resulted in formation of crystals.

The XRPD pattern of the obtained crystals of form B is shown in FIG. 1.

In addition, a suitable single-crystal of form B was selected under the microscope and was analyzed by means of single-crystal x-ray diffraction (SCXRD). The obtained data are represented above in the section preceding the examples.

Example 9—Preparation of Crystalline Form a (Reference)

About 5 g treosulfan were dissolved in about 80 g of 2-propanol under stirring at 65° C. The resulting solution was then filtered using a 0.2 μm filter and cooled to 15° C. which resulted in the precipitation of crystals. The crystals were collected and dried at about 40° C.

Figure 2:
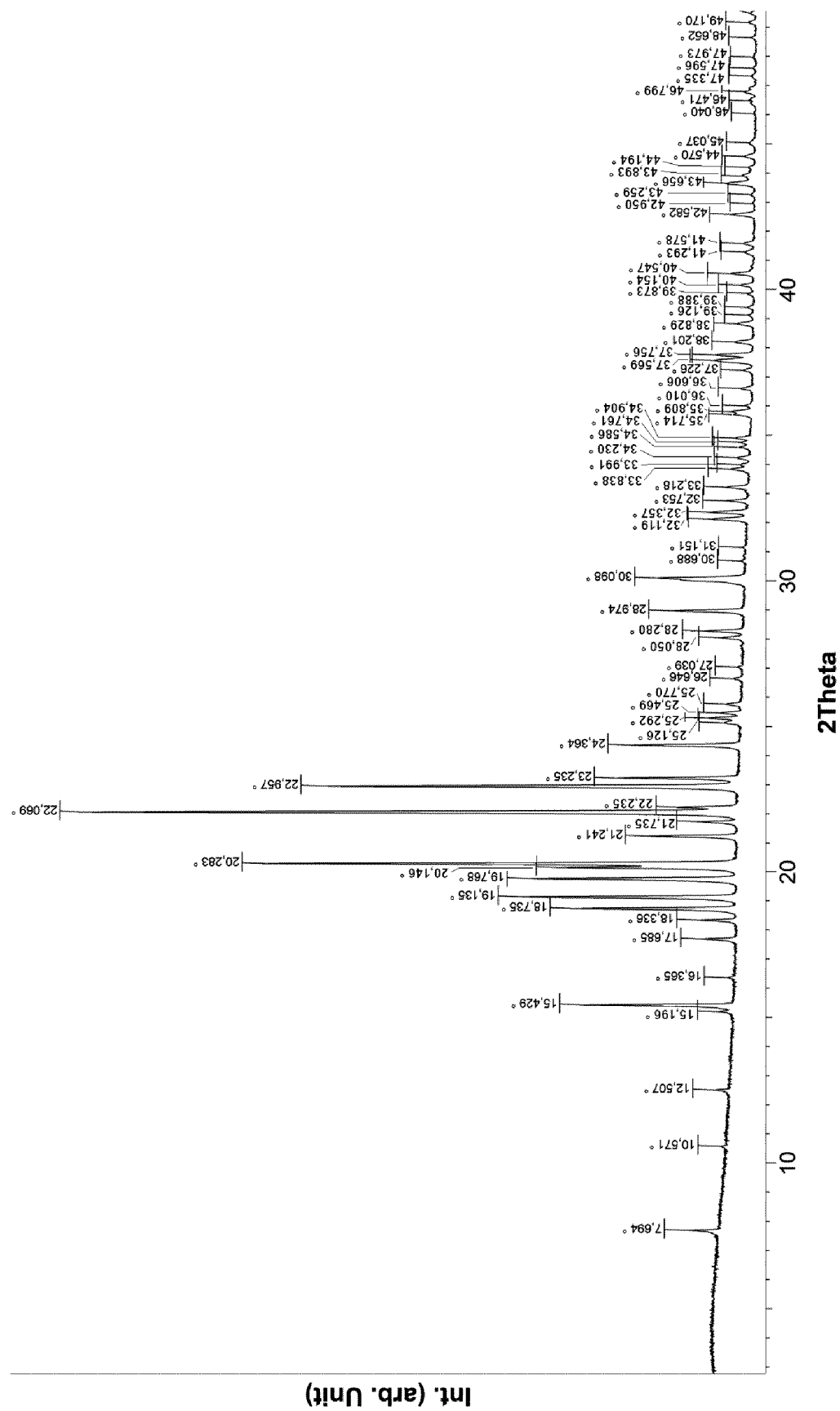
FIG. 2 shows an XRPD pattern of crystals of crystalline form A of treosulfan.

The XRPD pattern of the dried crystals is shown in FIG. 2 and confirms it to be crystalline form A of treosulfan. The crystalline form A exhibits an XRPD pattern having characteristic peaks at 7.69, 15.43, 18.74, 19.14, 19.77, 20.15, 20.28, 21.24, 21.74, 22.07, 22.96, 23.24, 24.36, 25.29, 28.05, 28.28, 28.97, 30.10 and 40.55±0.20 degrees 2Θ.

In addition, a suitable single-crystal of form A was selected under the microscope and was analyzed by means of single-crystal x-ray diffraction (SCXRD). The obtained data are represented above in the section preceding the examples.

The invention claimed is:

1. A lyophilisate of treosulfan, wherein the lyophilisate comprises crystalline form B of treosulfan exhibiting an X-ray powder diffraction pattern having characteristic peaks at 20.87 and 23.47±0.20 degrees 2Θ.

2. The lyophilisate according to claim 1, wherein the crystalline form B exhibits an X-ray powder diffraction pattern having characteristic peaks at 20.87, 23.47, 26.20, 29.65, 30.81, 34.54, 35.30, 36.87 and 46.24±0.2 degrees 2Θ.

3. The lyophilisate according to claim 1, wherein the crystalline form B exhibits an X-ray powder diffraction pattern essentially as shown in FIG. 1.

4. The lyophilisate according to claim 1, wherein the crystalline form B exhibits an X-ray powder diffraction pattern having no peaks in at least one of the following regions a to f, expressed as degrees 2Θ:

| Region | Degrees 2Θ |
|---|---|
| a | 19.00-19.50 |
| b | 20.00-20.65 |
| c | 21.50-23.21 |
| d | 23.75-24.95 |
| e | 27.40-28.35 |
| f | 30.00-30.60 |

5. The lyophilisate according to claim 1, which comprises at least 96% by weight of the crystalline form B, relative to the combined amount of crystalline form B and crystalline form A.

6. The lyophilisate according to claim 1, which comprises at least 75% by weight of the crystalline form B, relative to the amount of lyophilisate.

7. The lyophilisate according to claim 1 which comprises less than 20% by weight of amorphous phase, relative to the amount of lyophilisate.

8. The lyophilisate according to claim 1, which comprises at least 95% by weight of treosulfan.

9. The lyophilisate according to claim 1, which comprises less than 0.2% by weight of methanesulfonic acid.

10. The lyophilisate according to claim 1, which comprises less than 1% by of water.

11. The process for preparing the lyophilisate according to claim 1, which process comprises freeze-drying an aqueous solution comprising treosulfan.

12. The process according to claim 11, wherein the aqueous solution comprises water and optionally one or more organic solvents.

13. The process according to claim 12, wherein the organic solvent is acetic acid.

14. The process according to claim 11, which comprises
 (a) providing the aqueous solution having a first temperature,
 (b) freezing the aqueous solution, wherein the aqueous solution is cooled from the first temperature to a freezing temperature at a cooling rate of not more than 3 K/min, and
 (c) drying the frozen solution obtained in step (b) to give the lyophilisate.

15. The process according to claim 14, wherein the cooling rate in step (b) is not more than 2 K/min.

16. The process according to claim 11, wherein the first temperature is from 15° C. to 95° C.

17. The process according to claim 11, wherein the freezing temperature is −40° C. or less.

18. The process according to claim 11, wherein the frozen solution is kept at the freezing temperature for at least 1 hour.

19. The process according to claim 14, wherein the drying in step (c) includes a primary drying which is carried out by subjecting the frozen solution to a temperature of −25° C. or higher and subjecting the frozen solution to a pressure of 0.03 to 1.0 mbar,
or
the drying in step (c) includes a primary drying which is carried out by subjecting the frozen solution to a temperature of 0° C. or higher and subjecting the frozen solution to a pressure of 0.03 to 1.0 mbar.

20. The process according to claim 19, wherein the primary drying is carried out for at least 5 hours.

21. The process according to claim 19, wherein after the primary drying a secondary drying is carried out by subjecting the product of the primary drying to a temperature of at least 30° C. and subjecting the product of the primary drying to a pressure of 0.03 to 1.0 mbar.

22. A method of treating cancer comprising preparing a pharmaceutical composition from the lyophilisate according to claim 1 and administering the pharmaceutical composition to a patient suffering from cancer.

23. A method comprising preparing a pharmaceutical composition from the lyophilisate according to claim 1 and administering the pharmaceutical composition to a patient in need thereof as a conditioning therapy before transplantation of bone marrow or of blood stem cells into the patient.

* * * * *